United States Patent
Alhaqan

(10) Patent No.: US 9,439,648 B1
(45) Date of Patent: Sep. 13, 2016

(54) SUTURE PASSER WITH RETRACTABLE NEEDLE SHEATH

(71) Applicant: Salem A. Alhaqan, Safat (KW)

(72) Inventor: Salem A. Alhaqan, Safat (KW)

( * ) Notice: Subject to any disclaimer, the term of this patent is extended or adjusted under 35 U.S.C. 154(b) by 0 days.

(21) Appl. No.: 15/092,579

(22) Filed: Apr. 6, 2016

(51) Int. Cl.
*A61B 17/04* (2006.01)
*A61B 17/00* (2006.01)

(52) U.S. Cl.
CPC ....... *A61B 17/0493* (2013.01); *A61B 17/0469* (2013.01); *A61B 17/0483* (2013.01); *A61B 2017/00349* (2013.01)

(58) Field of Classification Search
CPC .......... A61B 17/0469; A61B 17/0483; A61B 17/0493; A61B 2017/0349
See application file for complete search history.

(56) References Cited

U.S. PATENT DOCUMENTS

| | | | |
|---|---|---|---|
| 3,205,863 A | 9/1965 | Rhoades | |
| 5,261,917 A * | 11/1993 | Hasson | A61B 17/0469 606/139 |
| 5,766,217 A * | 6/1998 | Christy | A61B 17/12013 606/139 |
| 5,797,928 A * | 8/1998 | Kogasaka | A61B 17/0469 606/139 |
| 5,944,739 A | 8/1999 | Zlock et al. | |
| 8,435,253 B2 | 5/2013 | Niese et al. | |
| 2005/0154403 A1 * | 7/2005 | Sauer | A61B 17/0469 606/139 |
| 2005/0209612 A1 | 9/2005 | Nakao | |
| 2007/0213745 A1 * | 9/2007 | Takemoto | A61B 17/0469 606/144 |
| 2007/0225736 A1 * | 9/2007 | Zeiner | A61B 17/04 606/148 |
| 2008/0033458 A1 * | 2/2008 | McLean | A61F 2/0063 606/144 |
| 2010/0087857 A1 * | 4/2010 | Stone | A61B 17/0401 606/232 |
| 2014/0128889 A1 | 5/2014 | Sullivan et al. | |
| 2015/0094739 A1 | 4/2015 | Norton et al. | |
| 2015/0230789 A1 | 8/2015 | Wales et al. | |

FOREIGN PATENT DOCUMENTS

CN 203436355 2/2014

* cited by examiner

*Primary Examiner* — Alexander Orkin
(74) *Attorney, Agent, or Firm* — Richard C. Litman

(57) ABSTRACT

The suture passer with retractable needle sheath has an elongate housing with a handle extending generally radially from its proximal end. A hollow suture needle is affixed to the handle and extends through the housing to its opposite distal end. A selectively retractable and extendible needle sheath resides in the housing and is disposed about the needle. The sheath is extended over the needle tip to preclude inadvertent damage to internal organs during endoscopic surgery. The sheath is operated by a linear slide disposed externally to the housing. The sheath retraction and extension mechanism is similar to that used in retractable tip ball point pens. A tensile wire extends through the hollow needle, to manipulate a suture grip extending from the side of the needle adjacent the needle tip. A pivotally attached lever extends from the handle and is connected to the tensile wire for manipulating the suture grip.

6 Claims, 4 Drawing Sheets

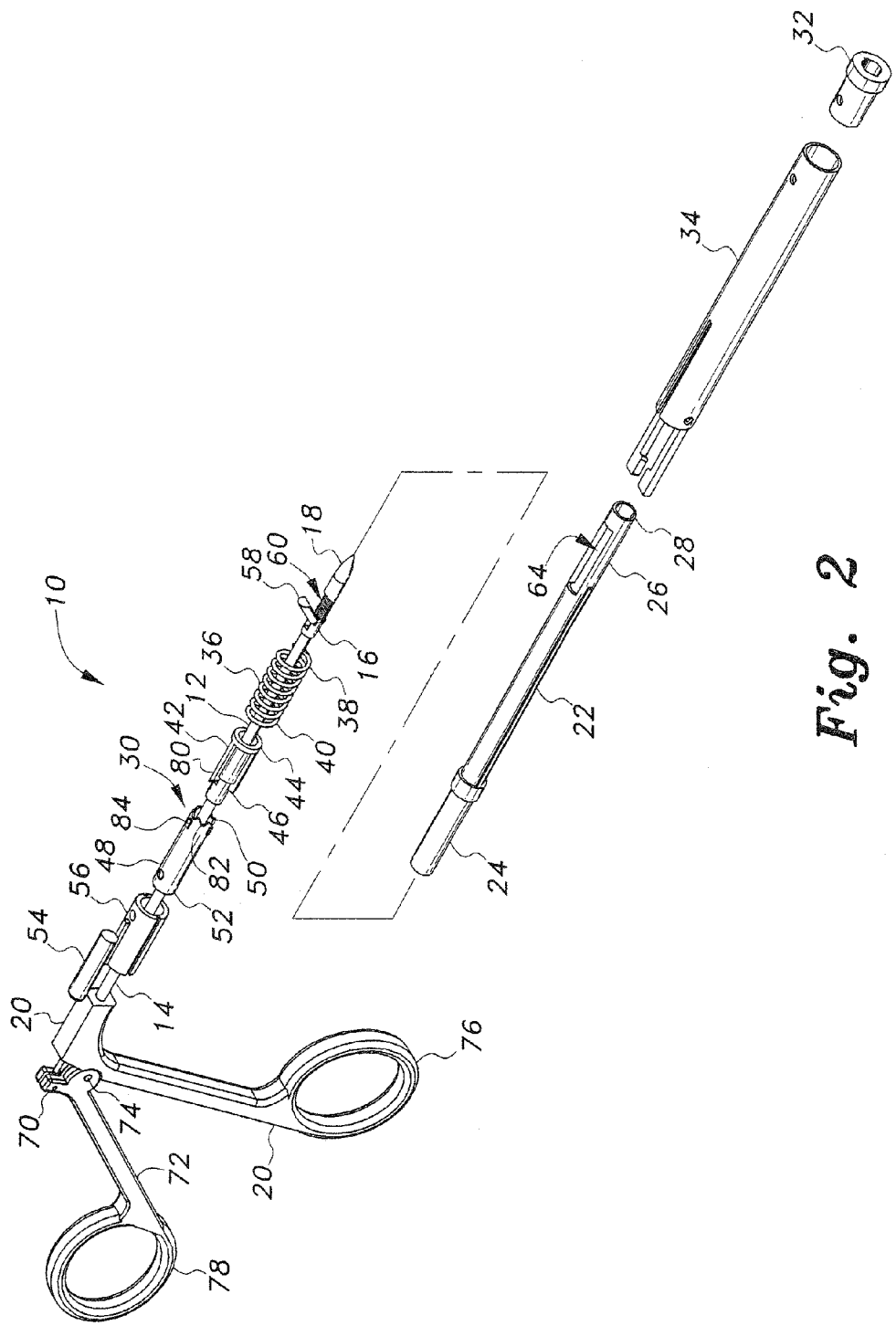

SUTURE PASSER WITH RETRACTABLE NEEDLE SHEATH

BACKGROUND OF THE INVENTION

1. Field of the Invention

The present invention relates generally to the medical device, and more particularly to a suture passer with retractable needle sheath that permits a medical practitioner to selectively expose the needle as needed or to cover the needle tip to prevent accidental damage to ancillary tissues when performing surgery.

2. Description of the Related Art

Endoscopic surgery is a relatively newly developed surgical technique that reduces the size of access openings that are necessary to be cut in the body of the patient, and thus greatly reduces the risks involved in surgical procedures. Endoscopic surgery involves the use of manipulative surgical instruments that are capable of performing various incising, cauterizing, stitching, and other operations within a bodily cavity while being manipulated remotely by the surgeon. The opening in the body is created generally via the umbilicus for abdominal operations, in order to minimize surgical trauma to the patient and to minimize post-operative scarring.

One of the surgical instruments used in such procedures is the stitch passer, a device that is used to close various abdominal layers (peritoneum, etc.) by stitching during laparoscopic surgery. Such stitch passers generally have a relatively sharp needle at their distal ends, for penetrating tissue in order to pass a suture through the tissue. This technique clearly requires a highly experienced and skilled surgeon capable of working through an umbilical or other small incision. Even so, it is possible for the surgeon to inadvertently puncture or otherwise damage an internal organ (intestine, etc.) when performing some other surgery (appendectomy, etc.) due to the exposed sharp tip of the stitch passer needle.

Endoscopic suture passers having exposed needles have been developed in the past, as noted further above. An example of such is found in Chinese Patent Publication No. 203436355 published on Feb. 19, 2014 to Meng Qinghua. This reference describes (according to the drawings, English abstract, and English machine translation) a suture and knot-tying device having an outer tube, a retractable and extendible inner tube, and a needle sleeve disposed within the front end of the inner tube. The rear portion of a suture needle is disposed within the needle sleeve, with the forward portion of the needle extending therefrom.

Thus, a suture passer with retractable needle sheath solving the aforementioned problems is desired.

SUMMARY OF THE INVENTION

The suture passer with a retractable needle sheath comprises a narrow, elongate device having mutually opposed proximal and distal ends. A handle extends generally radially from the proximal end and is immovably affixed thereto. A lever is pivotally attached to the immovably affixed handle.

A long, narrow housing extends forwardly from the handle. A thin, elongate surgical needle is immovably affixed to the handle, and extends forwardly therefrom through the housing. A selectively retractable and extendible needle sheath is disposed about the needle, and may be extended to cover the tip of the needle in order to preclude inadvertent damage to the patient's tissues during surgical operations. The needle sheath is operated by a push button extending from the side of the housing, adjacent the handle. The sheath extension and retraction mechanism is similar to that of a retractable tip ball point pen.

The needle is hollow, with a tensile wire extending therethrough from the lever of the handle to a suture grip that is selectively extendible from the needle adjacent its distal tip. The lever is used to draw the wire in order to close the suture grip to the needle, thereby gripping a suture therein. Release of the lever permits the grip to open, thereby releasing the suture.

These and other features of the present invention will become readily apparent upon further review of the following specification and drawings.

BRIEF DESCRIPTION OF THE DRAWINGS

FIG. 2 is an exploded perspective view of the suture passer with a retractable needle sheath according to the present invention, illustrating the internal components thereof and their relationships to one another.

Similar reference characters denote corresponding features consistently throughout the attached drawings.

DETAILED DESCRIPTION OF THE PREFERRED EMBODIMENTS

Figure 1:
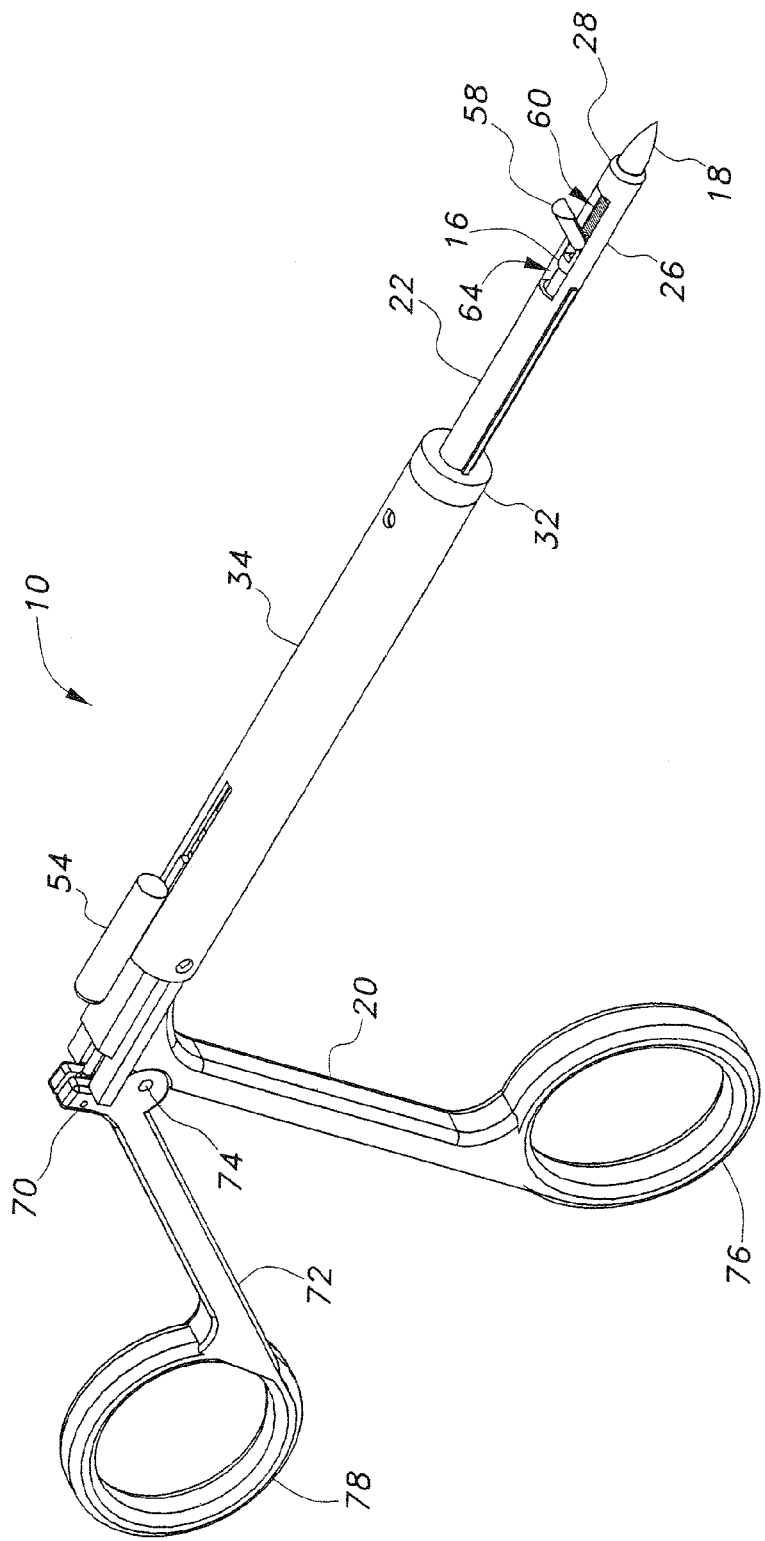
FIG. 1 is a perspective view of a suture passer with retractable needle sheath according to the present invention, illustrating its general features.

The suture passer with a retractable needle sheath is an endoscopic surgical instrument having a distal suture needle and suture grip, with a needle sheath that can be selectively extended to cover the needle tip to preclude inadvertent injury to internal organs or retracted to expose the needle tip during the suturing procedure. FIG. 1 of the drawings provides a perspective view of the suture passer with retractable needle sheath, or suture passer, 10, with FIG. 2 providing an exploded perspective view. The suture passer 10 includes a thin, elongate, hollow suture needle 12 (FIG. 2) having a proximal end 14, an opposite distal portion 16, and a sharp distal needle tip 18 extending from the distal portion 16. A handle 20 extends generally radially from the needle and other components concentric therewith, with the proximal end 14 of the needle 12 being immovably affixed to the handle 20. An elongate, hollow needle sheath 22 is disposed concentrically about the needle 12. The needle sheath 22 includes a proximal end 24, an opposite distal portion 26 disposed about the distal portion 16 of the needle 12, and a distal tip 28.

Figure 3A:
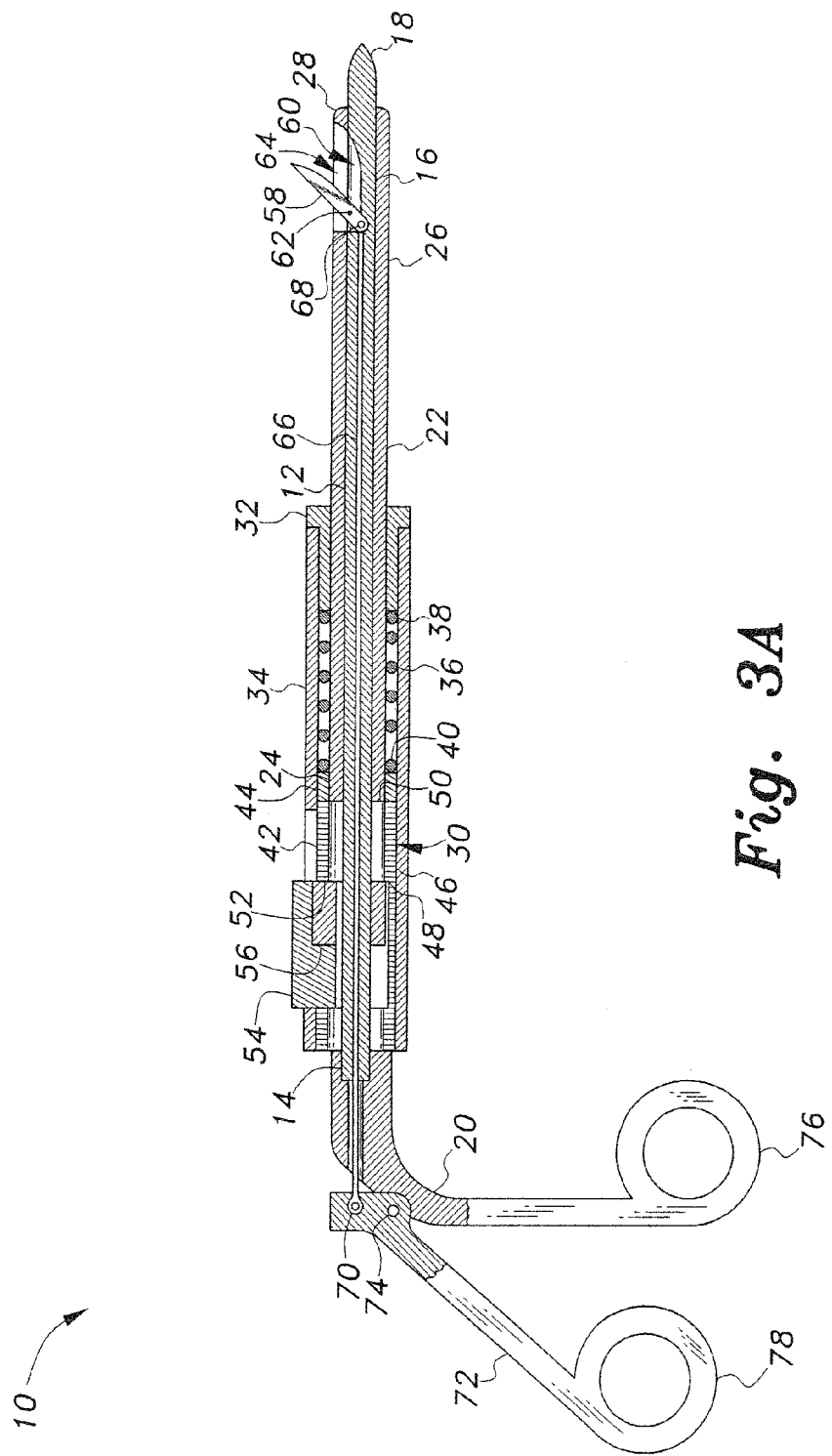
FIG. 3A is a right side elevation view in partial section of the suture passer with a retractable needle sheath according to the present invention, showing the instrument with the suture grip extended and the needle sheath retracted.
Figure 3B:
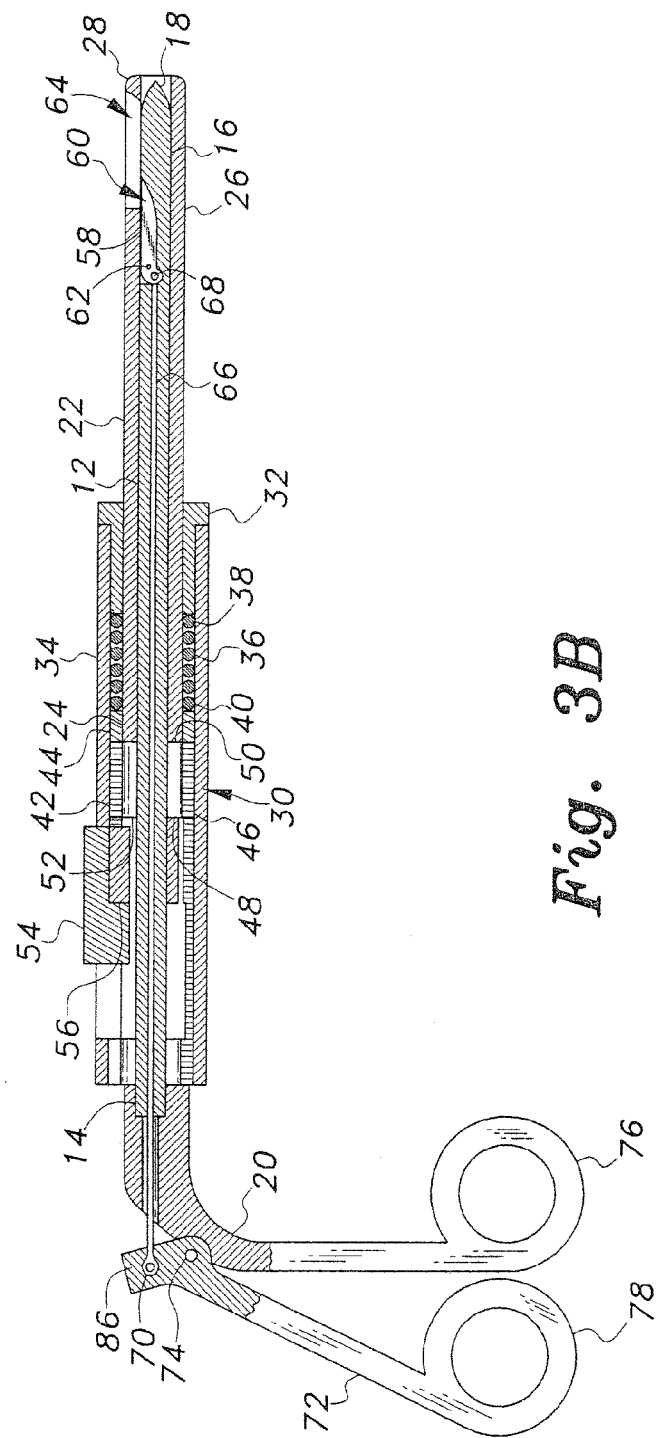
FIG. 3B is a right side elevation view in partial section of the suture passer with a retractable needle sheath according to the present invention, showing the instrument with the suture grip retracted and the needle sheath extended.

The needle sheath 22 is selectively extended over the needle tip 18 or retracted to expose the needle tip 18 by a sheath actuator mechanism 30 with which the needle sheath 22 communicates. FIG. 2 provides a detailed view of the various components of the actuator mechanism 30, with FIGS. 3A and 3B illustrating the needle sheath 22 in its retracted state and FIG. 3B illustrating the needle sheath 22 in its extended position to cover the needle tip 18. The actuator mechanism 30 is operated by a spring and cam mechanism disposed concentrically with the needle sheath 22. A spring seat 32 is disposed concentrically about the needle sheath 22, with the sheath 22 selectively extending and retracting through the center of the spring seat 32. The spring seat 32 is immovably affixed in the distal end of an elongate housing 34 that is disposed concentrically about the suture needle 12, the needle sheath 22, and the sheath actuator mechanism 30, with the proximal end of the housing 34 being immovably affixed to the handle 20.

A coiled compression spring 36 is disposed concentrically about the needle sheath 22 adjacent to the proximal end 24 thereof. The spring 36 has a distal end 38 that bears against the spring seat 32, and an opposite proximal end 40. A generally cylindrical cam follower 42 having a distal flange 44 is immovably affixed about the needle sheath 22, with the proximal end 40 of the spring 36 bearing against the distal flange 44 of the cam follower 42. The cam follower 42 further includes a proximal end 46 comprising a plurality of axially disposed fingers 80 that in turn bear against a generally cylindrical cam 48 disposed concentrically about the needle 12. The cam 48 has a distal end 50 comprising a plurality of circumferential ramps 82 and slots 84 of varying depths that engage the fingers of the proximal end 46 of the cam follower 42, and an opposite proximal end 52.

A sheath actuator button 54 extends radially from the needle sheath 22 through an axial slot in the housing 34, and communicates with the needle sheath 22 and the proximal end 52 of the cam 48 by means of a sleeve 56 that engages the proximal end 52 of the cam 48. Actuation of the sheath actuator button 54 alternatingly causes the cam 48 to rotate incrementally about the needle 12, thereby positioning the ends of the fingers of the cam follower 42 upon either high lobes or in slots of the cam 48 to retract (FIG. 3A) and extend (FIG. 3B) the needle sheath 22. This mechanism is generally related to that used for the extension and retraction of the tip of a retractable ball point pen. An exemplary mechanism is described in U.S. Pat. No. 3,205,863 issued on Sep. 14, 1965 to N. K. Rhoades, incorporated herein by reference.

The suture passer with retractable needle sheath 10 further includes a selectively operable suture grip 58 disposed in the distal portion 16 of the needle 12, shown generally in FIGS. 1 and 2 and in greater detail in FIGS. 3A and 3B. A suture grip recess 60 is formed in the distal portion 16 of the needle 12, with the suture grip 58 being pivotally secured therein by a pivot pin 62. The suture grip 58 can extend radially from the suture grip recess 60 through a passage 64 formed in the distal portion 26 of the needle sheath 22. A suture grip actuator wire 66 extends axially through the center of the hollow needle 12, and has a distal end 68 terminating at a pivot attaching the actuator wire 66 to the suture grip 58. The opposite proximal end 70 of the suture grip actuator wire 66 extends through the upper portion of the handle 20 beyond the proximal end 14 of the needle 12 and terminates in at the distal end 86 of the lever 72. The actuator wire 66 is pivotally attached to the suture grip actuator lever 72, with the lever 72 in turn being pivotally attached to the handle 20 by a pivot 74. It will be seen that squeezing the suture grip actuator lever 72 toward the fixed handle 20 results in the suture grip actuator wire 66 being drawn rearwardly, i.e., in a proximal direction, to draw the suture grip 58 into the suture grip recess 60 of the needle 12. As such, a suture is gripped between the suture grip 58 and the distal portion 16 of the needle 12, generally as shown in FIG. 3B. Both the handle 20 and the suture grip actuator lever 72 include finger loops, respectively 76 and 78, at their distal ends to facilitate manipulation of the suture passer 10.

Accordingly, the suture passer with retractable needle sheath 10 provides not only for the remotely operable selective grip and release of a suture in endoscopic surgery, but also allows the surgeon to extend a protective sheath over the sharp tip of the suture needle when the needle is not specifically in use. Thus, the needle is precluded from inadvertent penetration or puncture of an internal organ during surgery, thus greatly enhancing the safety of the surgical operation.

It is to be understood that the present invention is not limited to the embodiments described above, but encompasses any and all embodiments within the scope of the following claims.

I claim:

1. A suture passer with retractable needle sheath, comprising:

an elongate hollow suture needle having a proximal end and a distal portion opposite the proximal end, with a sharp distal tip, extending from the distal portion;

a handle immovably affixed to the proximal end of the suture needle;

an elongate, hollow needle sheath concentrically disposed about the suture needle, the needle sheath having a proximal end and a distal portion opposite the proximal end, with a distal end extending from the distal portion, the distal portion of the needle sheath being disposed about the distal portion of the suture needle and being immovably affixed to the handle;

a sheath actuator mechanism communicating with the needle sheath, the sheath actuator mechanism consisting of:

a spring seat disposed circumferentially about the needle sheath, the spring seat immovably affixed in the distal end of the hollow needle sheath;

a compression spring disposed about the needle sheath adjacent the proximal end thereof, the compression spring having a distal end bearing directly against the spring seat of the needle sheath and a proximal end opposite the distal end;

a cylindrical cam follower affixed about the needle sheath, the cam follower having a distal flange bearing directly against the proximal end of the compression spring and a proximal end opposite the distal flange, wherein the proximal end includes a plurality of axially disposed fingers;

a cylindrical cam, the cam having a distal edge directly engaging the proximal edge of the cam follower and a proximal edge opposite the distal edge, the cam includes a plurality of circumferential ramps and slots for engaging the plurality of axially disposed fingers; and a radially outwardly extending sheath actuator button, the actuator button directly engaging the cam, wherein the cam is forced to rotate about the needle thereby positioning the fingers upon either the ramps or slots, whereby the sheath actuator mechanism alternatingly extending the needle sheath such that the distal end of the needle sheath is disposed over the tip of the suture needle and retracting the needle sheath such that the tip of the suture needle extends beyond the distal end of the needle sheath.

2. The suture passer with retractable needle sheath according to claim 1, further comprising:

the distal portion of the suture needle having a suture grip recess disposed therein;

a suture grip pivotally disposed within the suture grip recess of the suture needle;

a suture grip actuator wire extending through the hollow suture needle, the suture grip actuator wire having a proximal end extending beyond the proximal end of the suture needle and a distal end opposite the proximal end, the distal end of the suture grip actuator wire being pivotally attached to the suture grip; and a suture grip actuator lever pivotally attached to the proximal end of the suture grip actuator wire, the suture grip actuator lever selectively operating the suture grip by means of the suture grip actuator wire.

3. The suture passer with retractable needle sheath according to claim 2, further comprising the suture grip actuator lever being pivotally attached to the handle.

4. The suture passer with retractable needle sheath according to claim 2, further comprising:

the handle having a distal end with a finger loop disposed thereon; and the suture grip actuator lever having a distal end with a finger loop disposed thereon.

5. The suture passer with retractable needle sheath according to claim 1, wherein the handle extends radially from the proximal end of the suture needle.

6. The suture passer with retractable needle sheath according to claim 1, further comprising an elongate housing disposed concentrically about the suture needle, the needle sheath, and the sheath actuator mechanism.

* * * * *